US011678841B1

(12) United States Patent
Jorgensen et al.

(10) Patent No.: US 11,678,841 B1
(45) Date of Patent: Jun. 20, 2023

(54) SYSTEM AND METHOD FOR SIMULATING OPIOID IMPAIRMENT

(71) Applicant: INNOCORP, LTD., Verona, WI (US)

(72) Inventors: Timothy Jorgensen, Madison, WI (US); Debra C. Kusmec-Aguilar, Verona, WI (US); Michael Aguilar, Verona, WI (US)

(*) Notice: Subject to any disclaimer, the term of this patent is extended or adjusted under 35 U.S.C. 154(b) by 257 days.

(21) Appl. No.: 17/106,540

(22) Filed: Nov. 30, 2020

(51) Int. Cl.
  *G08B 21/00* (2006.01)
  *A61B 5/00* (2006.01)

(52) U.S. Cl.
  CPC .......... *A61B 5/4845* (2013.01); *A61B 5/002* (2013.01); *A61B 5/6803* (2013.01)

(58) Field of Classification Search
  CPC ...... A61B 5/4845; A61B 5/002; A61B 5/6803
  USPC ....................................................... 340/573.1
  See application file for complete search history.

(56) References Cited

U.S. PATENT DOCUMENTS

| | | | | |
|---|---|---|---|---|
| 2005/0036110 | A1* | 2/2005 | Aguilar | G02C 7/16 351/159.17 |
| 2010/0259716 | A1* | 10/2010 | Kusmec-Aguilar | G02C 7/105 351/47 |
| 2011/0018719 | A1* | 1/2011 | Huang | G06Q 30/0283 340/573.1 |
| 2015/0194067 | A1* | 7/2015 | Kindschuh | G09B 19/0023 434/365 |
| 2018/0284100 | A1* | 10/2018 | Agu | A61B 5/4845 |
| 2020/0111259 | A1* | 4/2020 | Sears | G02B 27/0172 |

* cited by examiner

*Primary Examiner* — Mark S Rushing
(74) *Attorney, Agent, or Firm* — Quarles & Brady LLP (57) ABSTRACT

A system for demonstrating an effect of opioid compounds to a user. The system includes an eyewear device including at least one lens having an overlay affixed to at least a portion of the at least one lens, the overlay including a pattern that at least partially obscures a peripheral region of the at least one lens, and the at least one lens including a plurality of independently-controllable regions configured to be switched between different levels of opacity; a processor in communication with the eyewear device; and a memory in communication with the processor having stored thereon a set of instructions which, when executed by the processor, cause the processor to: transmit a plurality of signals to the eyewear device to switch at least one of the plurality of independently-controllable regions of the lens between the different levels of opacity.

21 Claims, 9 Drawing Sheets

SYSTEM AND METHOD FOR SIMULATING OPIOID IMPAIRMENT

BACKGROUND OF THE INVENTION

Opioids are highly addictive compounds which cause a spectrum of impairments in users. The United States has had an epidemic of opioid abuse for a number of years which worsened during the COVID-19 pandemic. One tool to reduce usage of and addiction to opioids is to teach the population about the impairments caused while using such compounds. While some teaching tools are known, none of the existing tools adequately provides a first-person experience which provides a user a feeling of the detrimental effects of opioid impairment.

SUMMARY OF THE INVENTION

The foregoing and other aspects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

In one embodiment the invention provides a system for demonstrating an effect of opioid compounds to a user. The system includes an eyewear device including at least one lens having an overlay affixed to at least a portion of the at least one lens, the overlay including a pattern that at least partially obscures a peripheral region of the at least one lens, and the at least one lens including a plurality of independently-controllable regions configured to be switched between different levels of opacity; a processor in communication with the eyewear device; and a memory in communication with the processor having stored thereon a set of instructions which, when executed by the processor, cause the processor to: transmit a plurality of signals to the eyewear device to switch at least one of the plurality of independently-controllable regions of the lens between the different levels of opacity.

In another embodiment the invention provides a method for demonstrating an effect of opioid compounds to a user. The method includes: providing an eyewear device including: at least one lens having an overlay affixed to at least a portion of the at least one lens, the overlay comprising a pattern that at least partially obscures a peripheral region of the at least one lens, and the at least one lens including a plurality of independently-controllable regions configured to be switched between different levels of opacity; and transmitting, by a processor in communication with the eyewear device, a plurality of signals to the eyewear device to switch at least one of the plurality of independently-controllable regions of the lens between the different levels of opacity.

The following detailed description includes references to the accompanying drawings, which form a part of the detailed description. The drawings show, by way of illustration, specific embodiments in which the apparatus may be practiced. These embodiments, which are also referred to herein as "examples" or "options," are described in enough detail to enable those skilled in the art to practice the present embodiments. The embodiments may be combined, other embodiments may be utilized or structural or logical changes may be made without departing from the scope of the invention. The following detailed description is, therefore, not to be taken in a limiting sense and the scope of the invention is defined by the appended claims and their legal equivalents. In this document, the terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation.

DETAILED DESCRIPTION OF THE INVENTION

Figure 1:
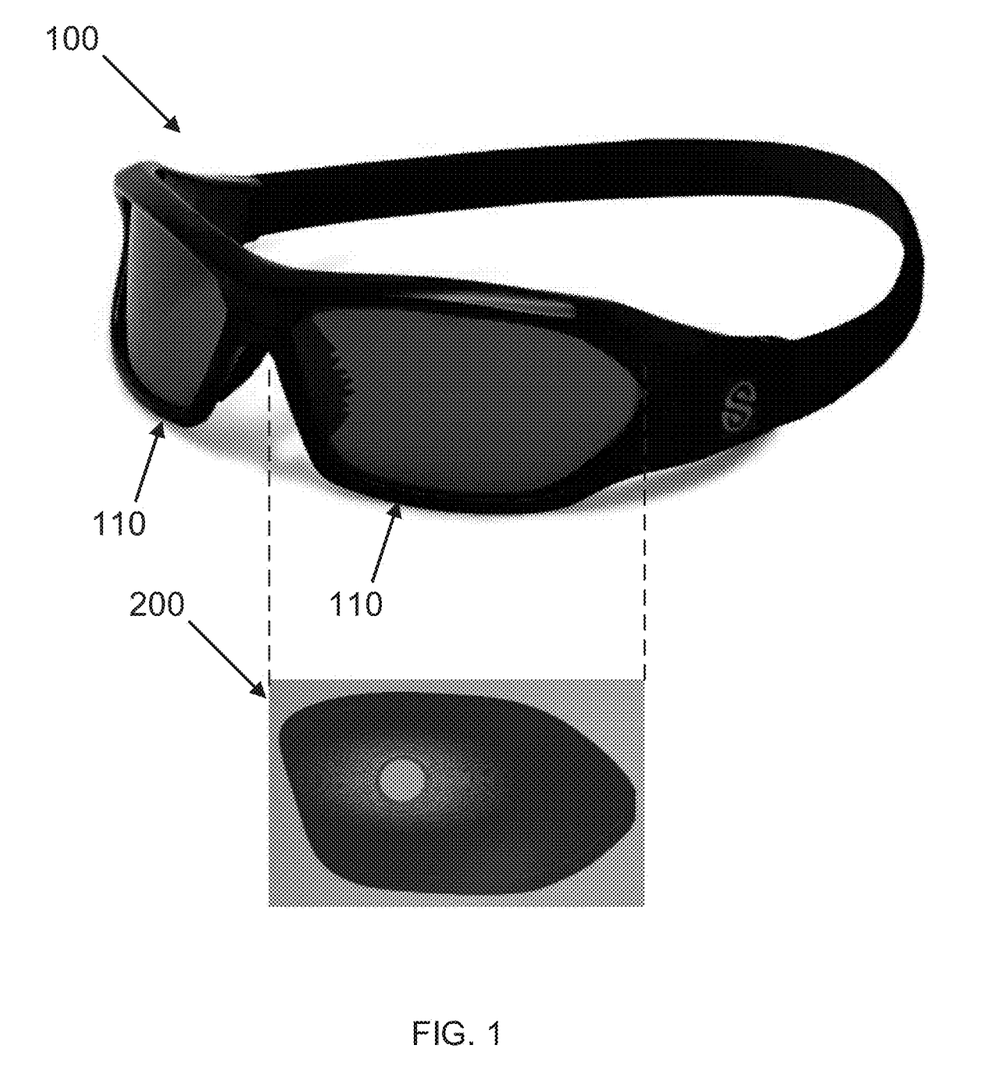
FIG. 1 shows an embodiment of an eyewear device (top) and an overlay (bottom).

Disclosed herein are systems, methods, and kits for demonstrating an effect of opioid compounds to a participant such as a student or other user. A system according to various embodiments may include an eyewear device 100 including at least one lens 110 having an overlay 200 affixed to at least a portion of the at least one lens 110, where the overlay 200 may include a pattern that at least partially obscures a region of the at least one lens 110 (FIG. 1). The top portion of FIG. 1 shows an embodiment of an eyewear device 100 having two lenses 110 and the bottom portion of FIG. 1 shows an embodiment of an overlay 200, with dashed lines indicating that the overlay 200 would be placed onto the lens 110. Another overlay that is a mirror image of the first overlay would be placed onto the other lens 110.

Figure 2:
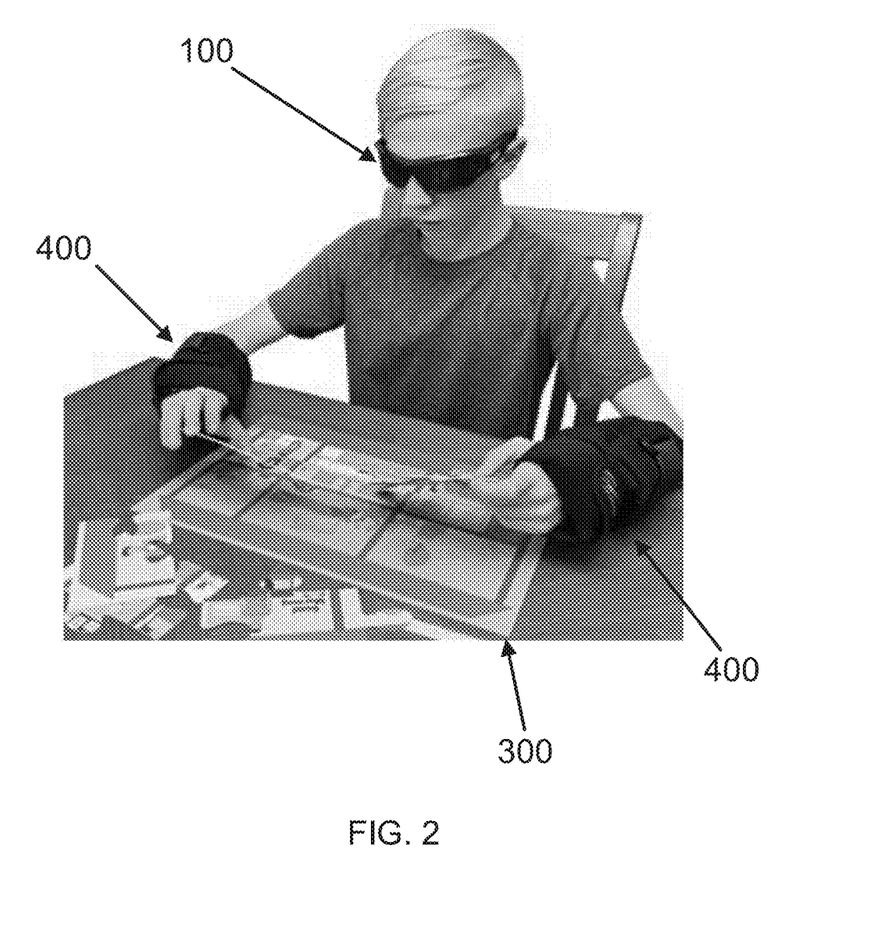
FIG. 2 shows a user wearing the eyewear device and weights on their wrists while performing an activity using the activity board.

As described further below, in various embodiments the eyewear device 100 may be used in conjunction with an activity board 300 in which a user wearing the eyewear device 100 may perform an activity while experiencing effects from a simulation of opioid use that is generated using the eyewear device 100 (FIG. 2). In some embodiments the user may additionally wear one or more weights 400, e.g. on the hands, wrists, or other parts of the arms, to enhance the simulated opioid experience by mimicking feelings of lethargy and heaviness that can be associated with opioid use (FIG. 2).

Embodiments of the disclosed systems, methods, and kits provide tools that can be used to raise awareness about the devastating impacts on the quality of life associated with the growing opioid crisis. Various embodiments demonstrate the impact of opioid impairment on a user's ability to function and the potential consequences associated with that impairment. The eyewear device 100 may be used in conjunction with activities on the activity board to help promote prevention and awareness initiatives to groups such as schools and in communities at large.

Certain embodiments help to simulate conditions including:

Divided Attention Failure, which may be characterized by a user's inability or struggle to sustain their focus in their present environment, which can result in difficulty managing and completing tasks;

Nodding Out, which may be characterized by a user who nods out is unresponsive to situations or cues that would typically drive a response and is often accompanied by a heaviness in extremities and an unconscious state;

Contrast Sensitivity Impairment, in which opioids can cause a user's pupils to constrict, resulting in impaired contrast sensitivity, leading to struggles with picking up on visual cues and responding appropriately; and Heaviness and Lethargy, in which opioids affect the respiratory system's intake of oxygen and slow the heart rate, which can result in slower movements, reduced strength, and a sense of heaviness in the extremities.

Figure 3:
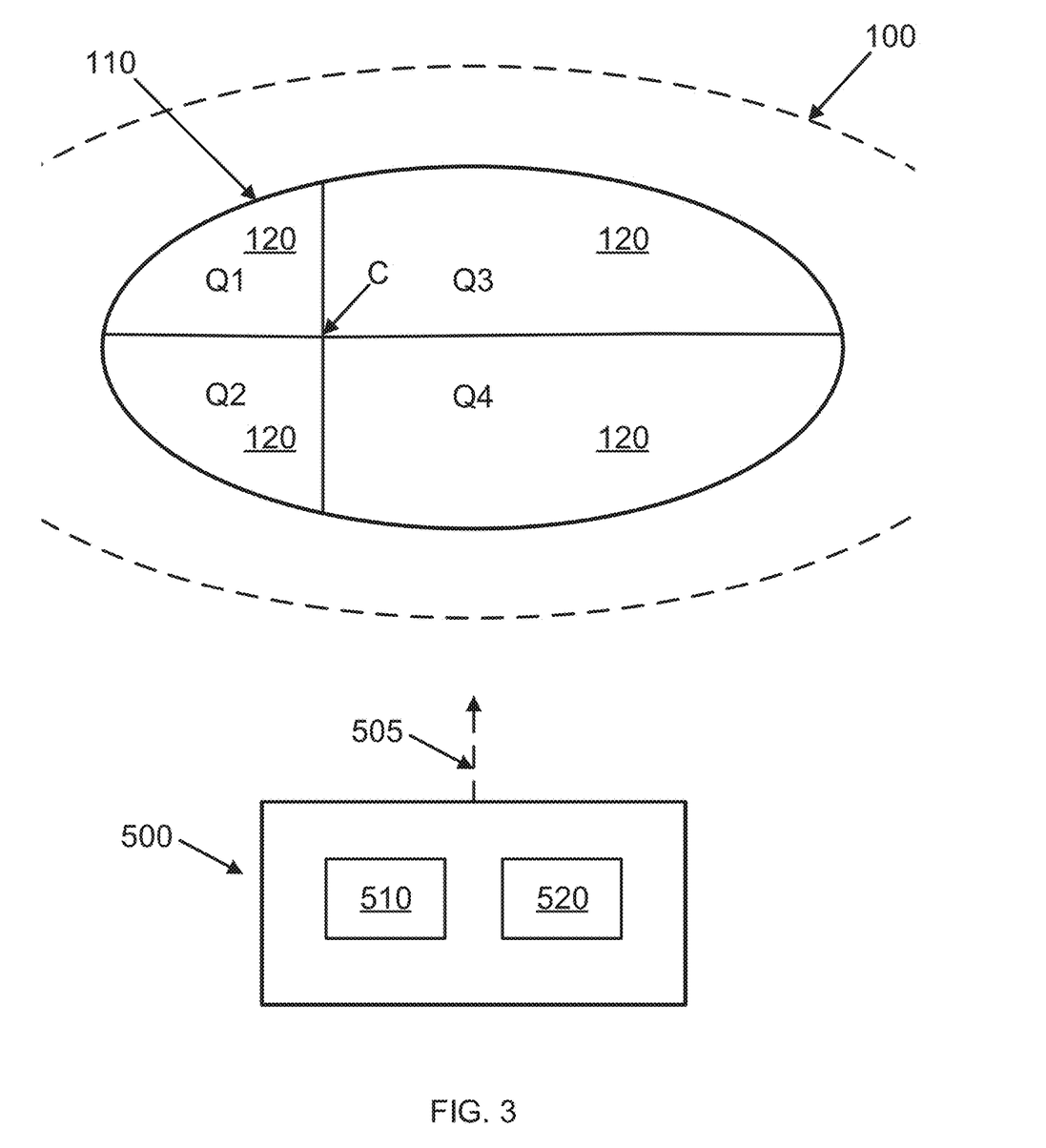
FIG. 3 shows a lens that has been divided into four independently-controllable regions Q1-Q4 in communication (e.g. wired or wireless) with a computer system.

The primary component of the simulated opioid experience is provided by the eyewear device 100, which includes one or more lenses 110 having regions that may be controlled to partially or completely obscure all or part of the viewing area as well as overlay(s) that may partially or completely obscure certain portions of the user's visual field. In one particular embodiment, the eyewear device 100 may be the Senaptec Quad Strobe eyewear by Senaptec, Inc., although other types of eyewear devices may also be used. The eyewear device 100 may include at least one lens 110, which can be a single lens that covers both eyes or two (or more) lenses components that cover both eyes. In certain embodiments, the at least one lens 110 may include (e.g. may be subdivided into) a plurality of independently-controllable regions 120 configured to be switched between different levels of opacity, for example between 0% to 100%. In some embodiments, the at least one lens may include a transparent state (0% opacity) and/or an opaque state (100% opacity), may have intermediate opacity levels between 0% and 100% that vary in 5% or 10% increments or other intermediate opacity levels. FIG. 3 shows a diagram of a single lens 110 (which is part of an eyewear device 100, shown with dashed lines) which has been divided into four independently-controllable regions 120 labeled Q1, Q2, Q3, and Q4. FIG. 3 also shows a computer system 500 in communication 505 (e.g. wired or wireless) with the eyewear device 100.

In various embodiments, the eyewear device 100 may be in communication with a processor 510 of the computer system 500, which itself may be in communication with or be integrally connected with a memory 520 (FIG. 3). In some embodiments, the eyewear device 100 may include a processor and/or memory and may be capable of controlling the lens 110 with varying levels of control from the external computer system 500. The memory 520 may have a set of instructions stored or loaded onto it which, when executed by the processor 510, cause the processor 510 to control the eyewear device 100. For example, the instructions may cause the processor 510 to transmit a plurality of signals to the eyewear device 100 to switch at least one of the independently-controllable regions 120 of the lens 110 between the different levels of opacity in the region.

The independently-controllable regions 120 of the lens 110 may be distributed in various patterns on the lens 110 and the lens 110 may be covered partially or completely with the independently-controllable regions 120. In one embodiment the independently-controllable regions 120 are divided into sectors that converge at or near a point C (FIG. 3) corresponding to the center of the field of vision for the person wearing the eyewear. For example there may be two sectors (e.g. left and right sides divided vertically or top and bottom regions divided horizontally), three sectors, four sectors (e.g. quadrants divided horizontally and vertically with the lines of division crossing at or near the center of the field of vision; see FIG. 3), or other numbers of sectors. The sectors may be divided into equal or unequal sizes and the lines of division between sectors may be at any angle. In other embodiments, the independently-controllable regions 120 may be distributed across the lens 110 as a series of squares or rectangles constituting multiple rows and columns. In still other embodiments, the independently-controllable regions 120 can form other patterns such as concentric regions including circular, oval, or other shaped regions or patterns. In some embodiments the multiple independently-controllable regions 120 may converge at a single point (e.g. center point C in FIG. 3) and this point may be aligned with the opening/region of lowest opacity in the associated overlays 200 applied to the lens 110.

The independently-controllable regions 120 may be created using various technologies such as those employing liquid crystal technologies or other electrically switchable optical materials. In various embodiments the materials may be disposed between transparent conductive layers that are patterned to produce a particular patterns such as any of those disclosed herein. When activated, the technology may produce complete opacity in the particular independently-controllable region 120 or may produce varying levels of opacity short of complete opacity, as discussed above.

In various embodiments the independently-controllable regions 120 may be controlled to activate and deactivate in various patterns in sequences which produce effects that help the user experience and gain understanding of some of the impacts of opioid use such as divided attention failure and nodding out. In certain embodiments the sequences may involve causing all of the independently-controllable regions 120 of one or both lenses 110 (in the case in which the eyewear includes two separate lenses) to become opaque at the same time to simulate nodding out. In particular embodiments the sequences may involve causing particular regions of the field of vision to become opaque at different times to simulate divided attention failure. In either of these simulations the user may experience the opacity sequences at the same time they are performing a particular task such as a task associated with an activity board 300 such as assembling a puzzle on the activity board 300 (see below). The simulated nodding out and/or divided attention failure generally impede the user as they try to perform the assigned task, such as assembling a puzzle, and thereby provide understanding to the user regarding the dangers of opioid use as well as the difficulties faced by those who use such compounds. In the case of an eyewear device 100 having two lenses 110 each of which is divided into four quadrants Q1-Q4 as shown in FIG. 3, nodding out can be simulated using an opacity sequence in which most or all of the independently-controllable regions 120 become opaque at the same time and divided attention failure can be simulated by having subsets (e.g. pairs of adjacent or diagonal regions) of the independently-controllable regions 120 become opaque at different times.

In some embodiments, the eyewear device 100 may include one lens 110 that is placed in front of both of a user's eyes and in other embodiments the eyewear device 100 may include two separate lenses 110, such that a different lens 110 is placed in front of each of the user's eyes. The lens or lenses 110 may include one or more overlays 200; for example when the eyewear device 100 has two lenses 110, each of the lenses 110 may include a separate overlay 200. The overlays 200 may include a pattern of varying colors or gray levels which may at least partially obstruct the eyesight of the participant, for example to simulate narrowed vision (e.g. from small/constricted pupils) experienced by some opioid addicts. In various embodiments, the pattern may be formed by concentric patterning such as a series of concentric lines of varying density and/or thickness which have the result of blocking most of the peripheral vision of the participant and only permitting vision in the center of the field of view (FIG. 4), where the densities may vary the opacity from 0% to 100%, e.g. in 5% or 10% increments. In other embodiments the altered field of view may be formed by providing a varying grayscale pattern which changes from black or near-black (i.e. completely or nearly completely opaque) at the periphery to clear (no opacity) in the center of the field of view, with a transition between the periphery and center that may be varied in a linear or non-linear manner or pattern.

In various embodiments, the overlays 200 may be applied to the lenses 110 and/or embedded into the lenses 110, e.g. during manufacture. For example, the overlays 200 may be applied to the lenses 110 using ink, dyes, or paint, and may be applied to an outer surface of the lenses 110 or to an intermediate layer. In some embodiments, the overlays 200 may be removably attached to the lenses 110, for example as adhesive stickers or as clings that can be reusably applied to the lenses 110. An advantage of using removable overlays 200 is that different overlay patterns may be attached for different users or to create different desired effects. Thus, different patterns may be provided on the overlays, for example with larger or smaller central openings or varying degrees of opacity in the peripheral regions. Nevertheless, in other embodiments the overlays may be applied to the lenses with an adhesive such that the overlays are not removable by the user and are permanent or semi-permanent (e.g. could not be removed by a user without damaging the lens).

Figure 4:
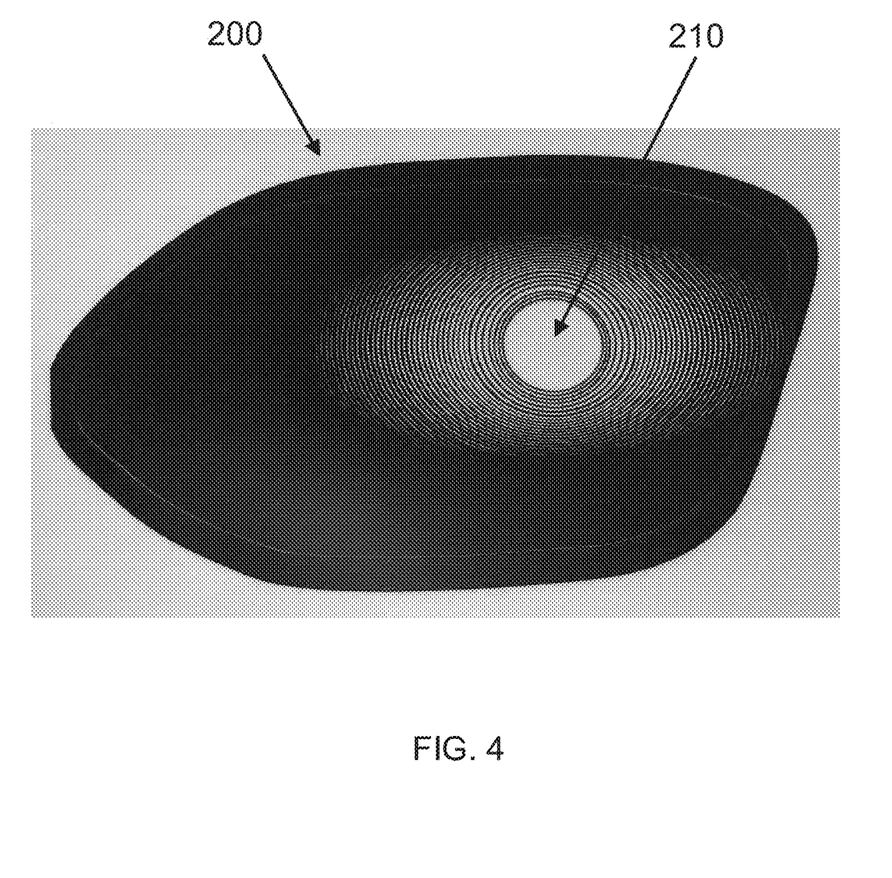
FIG. 4 shows an overlay with a series of concentric lines.

In certain embodiments, the overlays 200 include patterns that permit the user to see through the center of their field of view but which obstruct the peripheral regions of the viewing field (FIG. 4). In some embodiments, the concentric patterns on the overlays 200 are generated by providing a series of lines, e.g. concentric rings that may be circular, oval, or other regular or irregular shapes. The lines may vary in thickness and/or in their spacing/density such that the user is able to see relatively easily through the central portion of the field of vision but less easily through the peripheral portions of their field of vision. In particular embodiments, the central portion of the field of vision is unobstructed and the peripheral portions of the field of vision are completely obstructed, with a graded change in the level of obstruction in between the central and peripheral portions. The central portion of the pattern may have little or no obstructing material (e.g. ink, dye, paint, etc.) while the peripheral portions may be completely filled with obstructing material so that little or no light gets through.

As noted above, in some embodiments the variations in the level of obstruction provided by the overlays 200 may be produced by lines such as concentric rings of obstructing material. In other embodiments the variations in the level of obstruction may be produced using varying densities of obstructing material, for example to produce a variety of levels of obstruction to generate a "grayscale" effect. In still other embodiments the variations may be produced using patterns of obstructing material that vary in size and/or density per unit area, e.g. using halftones (i.e. dots or other structures that vary in size and/or density to simulate a continuous tone such as a grayscale effect). A halftone effect may be created using dots or as noted above a series of lines of varying thickness and/or spatial density, where the structure (dots, lines, or other structure) is generally made in a manner that is completely or nearly completely opaque.

Thus, the pattern of the overlay 200 may include a central opening 210 with little or no obstructing material, where the central opening may be positioned so that it is aligned with the central axis of the user's eye (e.g. point C in FIG. 3) and hence aligned with the center of the field of vision of the eye. Depending on the particular type of lens 110 with which the overlay 200 is associated, the central opening may be at or near the geometric center of the lens or may be located off-center on the lens 110 (e.g. closer to the centerline of the eyewear 100) so as to be aligned with the center of the field of vision (FIG. 4). For example, on lenses that extend relatively far to the side and curve towards a wearer's temples (e.g. wraparound glasses, see FIGS. 1, 2) the central opening 210 on the overlay 200 may be located away from the geometric center and closer to a region of the overlay 200 that would be located near the centerline of the eyewear 100 when the overlay 200 is associated with the eyewear 100.

The transition of the pattern of the overlay 200 from the area of little or no opacity in the central region 210 to the relatively high opacity in the peripheral regions may occur gradually with varying types of changes, such as a linear transition in opacity. In addition, the transition may be different in different directions, for example the transition region may be shorter and more abrupt in the vertical direction (vertical referring to the orientation when a user wearing the eyewear 100 is upright) compared to the horizontal direction (see FIG. 4). In some embodiments this may produce an approximately oval-shaped transition region just outside the central opening 210 in which the opacity transitions from clear/little opacity to highly opaque in the peripheral regions. As noted previously, the opacity pattern of the overlay 200 helps the user experience and gain understanding of some of the effects of using opioid compounds such as restricted vision, particularly contrast sensitivity, which can be related to pinning of the pupils.

Figure 5:
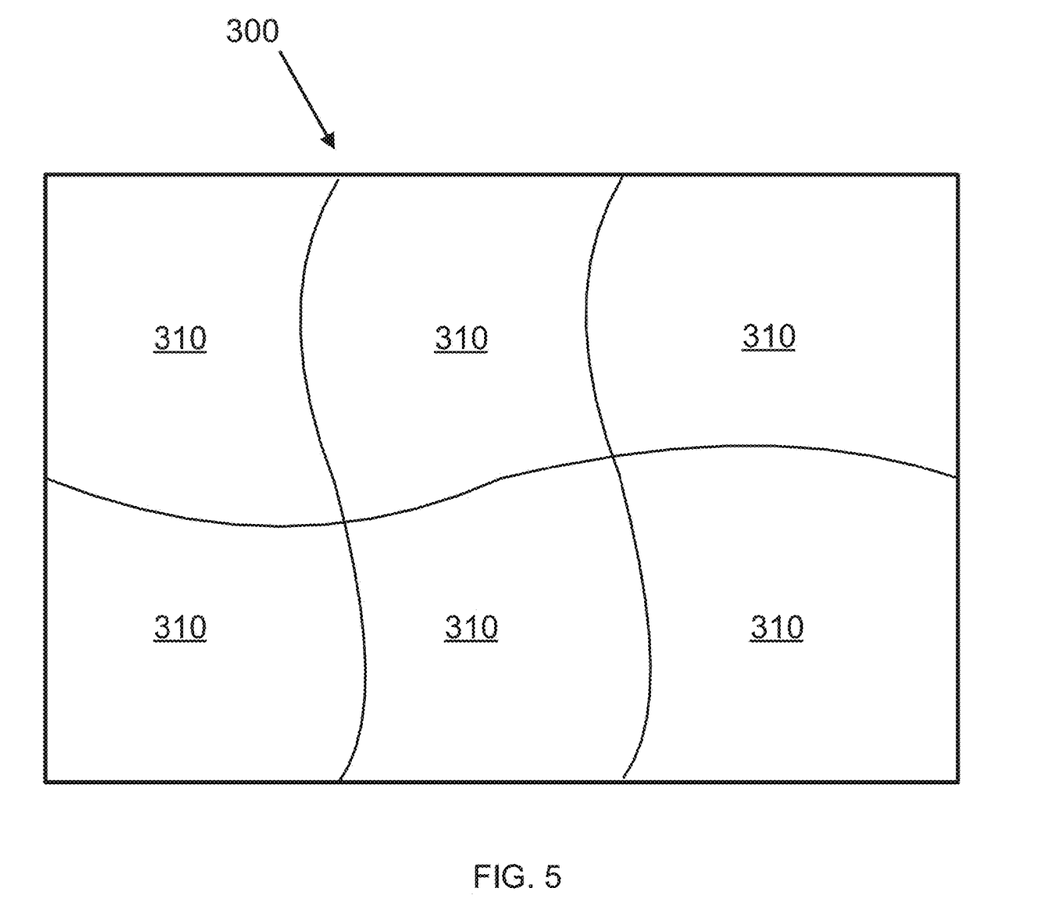
FIG. 5 shows an activity board upon which a six-piece puzzle has been assembled.

In various embodiments, the system may include an activity board 300 which can be used along with the eyewear device 100 (see FIGS. 2, 5). The activity board 300 may be used in a manner that helps to demonstrate to the participant the added difficulties that opioid users may face in carrying out daily activities. For example, in one embodiment the activity board 300 may resemble a cutaway diagram of a house which shows different regions of a typical residence, such as a kitchen, bedroom, living room, basement, laundry room, or other locations. In another embodiment the activity board 300 may resemble a school environment which shows different areas of a school, such as a classroom, a gymnasium, a cafeteria, a locker room, a library, or other locations, to provide particular relevance to students.

In one particular embodiment, the activity board 300 may also include tokens 310 such as puzzle pieces (e.g. 4-20 pieces and in one embodiment 6 pieces as shown in FIG. 5) which the participant may place on the activity board 300 while wearing the eyewear device 100. A facilitator may direct the user to place the tokens 310 on certain locations of the activity board 300 in a particular order or pattern. In certain embodiments in which the tokens 310 are puzzle pieces, the user may assemble the puzzle piece tokens 310 on the activity board 300 to complete a puzzle image that is similar to the pattern on the activity board 300 such that the assembled puzzle conveys a message to the user.

For example, the activity board 300 may depict a house which is organized and clean and whose occupants are contented, representing a home in which none of the occupants is addicted to opioids. On the other hand, the puzzle piece tokens 310 may assemble to form a different view of the home which is disorganized (e.g. dirty dishes piled in the kitchen sink and unwashed laundry accumulated in the laundry room) and whose occupants are neglected and unhappy, representing a home in which one or more occupants is addicted to opioids. In addition to the difficulties of assembling the puzzle with a simulated impairment from the eyewear 100, the activity board 300 and tokens 310 provide a visual depiction of the consequences of opioid abuse. In other embodiments the activity board 300 and tokens 310 may depict how the life of a student can be adversely affected by opioid addiction (see below).

In some embodiments the activity board 300 itself may depict the same or a similar home whose occupants are neglected and unhappy, representing a home in which one or more occupants is addicted to opioids, similar to the puzzle pieces. In addition, the puzzle piece tokens 310 may be printed on both sides such that one side of the pieces forms a portion of a picture of the non-opioid home and the reverse sides of the pieces may form portions of a picture of the non-opioid home or the opioid-afflicted home. Having images on both sides of the pieces adds to the challenge of assembling the puzzle since the pieces will correctly assemble only in one direction.

In another embodiment the activity board 300 may resemble a school environment which shows different areas of a school, such as a classroom, a gymnasium, a cafeteria, a locker room, a library, or other locations, to provide particular relevance to students. As with the previous example set in a home environment, the school-themed activity board 300 may include puzzle piece tokens 310 that depict similar school scenes in which a student's life is impacted by opioid use, for example by falling asleep in class, getting bad grades, or not being able to concentrate on studying, among other difficulties. The activity board 300 may be two-sided, with one side depicting a non-addicted student's school experience and the opposite side depicting the experiences of a student who is impacted by opioids. Similarly, the puzzle piece tokens 310 may be two-sided as well, depicting the non-addicted school experience on both sides or depicting the non-addicted and addicted school experiences on opposite sides, which as noted above increases the challenge of assembling the puzzle or completing other tasks on the activity board 300.

In various embodiments one or more weights 400 may be provided to a user who is wearing the eyewear device 100 as part of an experience to learn about the effects of opioids, particularly to create a sense of heaviness (particularly in the user's extremities) and lethargy that is sometimes experienced by opioid users. The weights 400 may be coupled to straps or bands (e.g. incorporated into a sleeve that can be secured to the hand or arm, for example using Velcro) to facilitate attaching the weights to the user's extremities (e.g. to wrists, forearms, ankles, or other body parts) to give the user a sense of their extremities being heavy and providing an overall sense of lethargy. The presence of the weights 400 on the user's arms while the user conducts an activity using the activity board 300 may further impede the user's progress during these exercises and thereby enhance the simulation of the effects of opioid use. The weights 400 may be between 1 pound and 5 pounds or other suitable weights selected to provide the user with a sense of heaviness and lethargy, particularly in their extremities, and the amount of weight that is provided to a particular user may be heavier or lighter depending on factors such as the age and size of the user.

Figure 6:
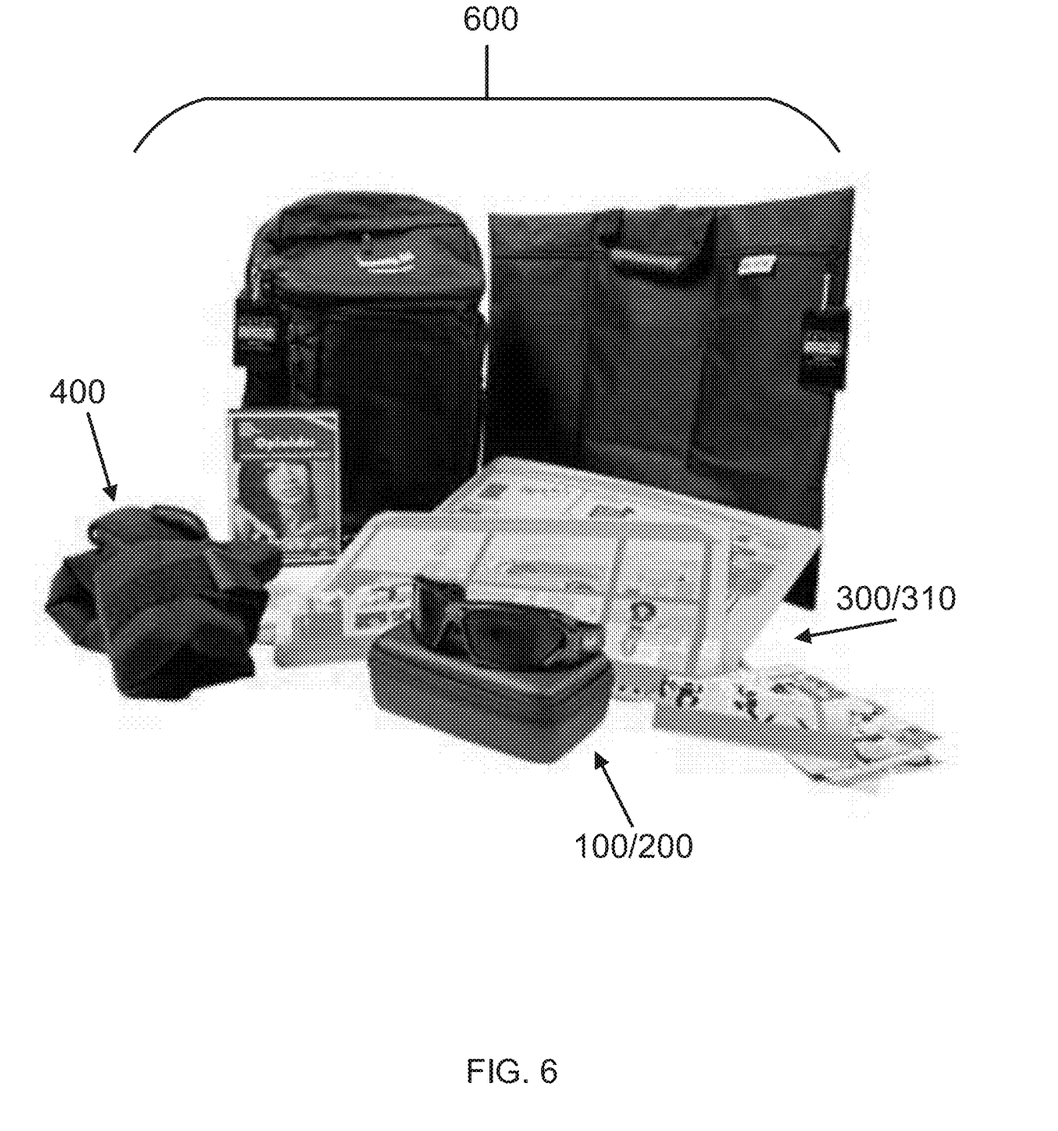
FIG. 6 shows a kit for demonstrating the effects of opioids on a user.

In certain embodiments a kit 600 may be provided which includes: the eyewear device 100 along with overlays 200; software to control the eyewear device; the activity board 300 and puzzle pieces or other tokens 310; and/or instructions (e.g. printed or in electronic form) for use of the kit to demonstrate the effects of opioids on a user's life (FIG. 6).

Figure 7:
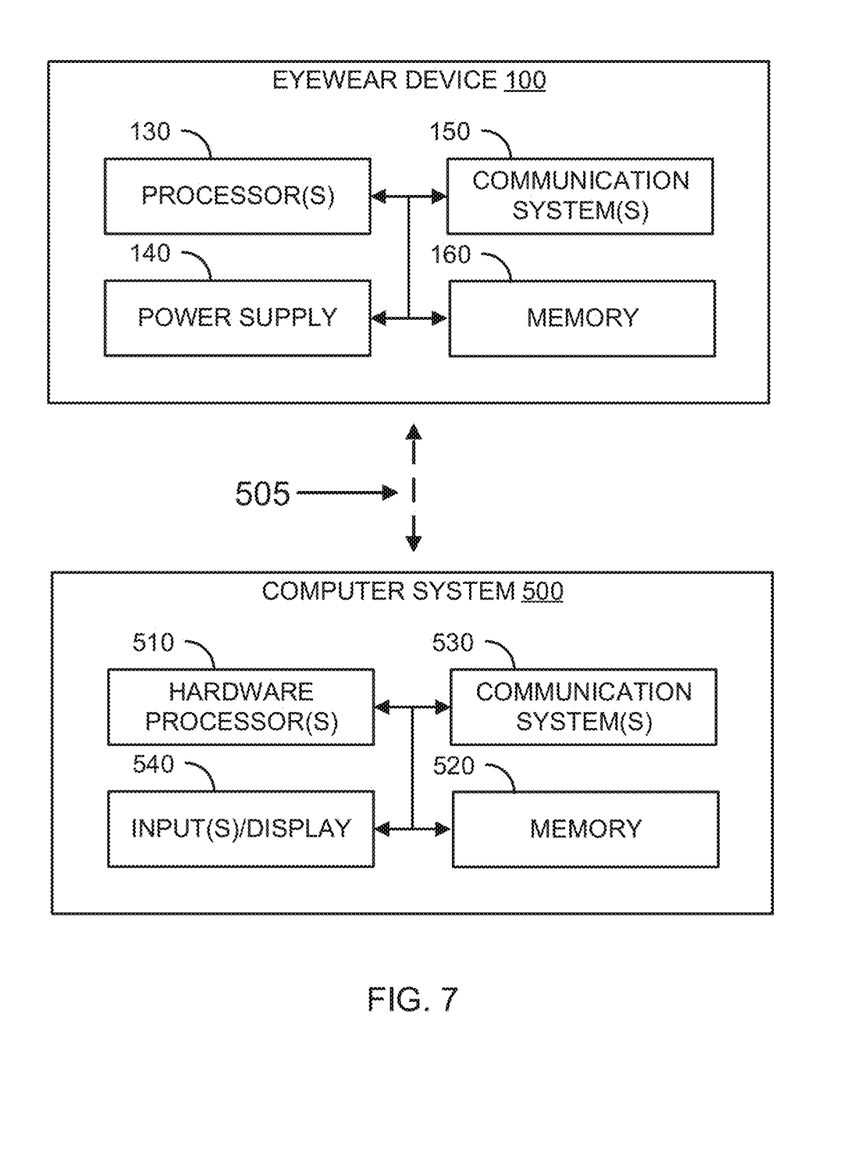
FIG. 7 shows a diagram of an eyewear device in communication with a computer system.

The eyewear device 100 may include a controller such as a processor 130, memory 160, a power supply 140 (e.g. a battery such as a rechargeable battery), and a communication system 150 (e.g. a wireless communication modality such as Bluetooth or a suitable wired communication mechanism) (FIG. 7). In some embodiments the eyewear device 100 may be self-contained and may be programmed to carry out various sequences of activation and deactivation of the various independently-controllable regions of the lens or lenses without requiring input or control from an external source. In other embodiments the eyewear device 100 may be programmed to carry out various sequences of activation and deactivation of the various independently-controllable regions 120 of the lens or lenses 110 which are initiated upon receipt of a signal from an external source. In still other embodiments the eyewear device 100 may not have the capability to carry out various sequences of activation and deactivation of the various independently-controllable regions 120 of the lens or lenses 110 and instead the sequences may be carried out based on a continuous series of individual commands that are sent to the eyewear device 100 from an external source.

Figure 8:
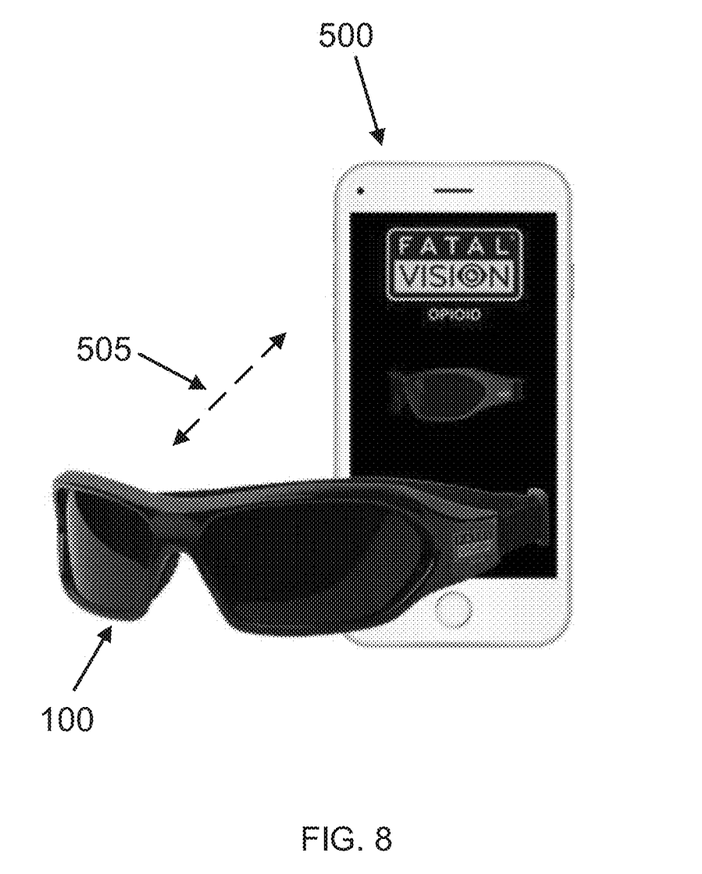
FIG. 8 shows a smartphone in communication with an eyewear device.

Thus, in various embodiments the software for controlling the eyewear device may be present on the eyewear device 100 itself, may be present on an external device, and/or may be distributed between the eyewear device 100 and one or more external devices. In certain embodiments the external device may include a standalone computer system 500, which may include a portable device such as a tablet, laptop computer, or a smartphone in communication 505 (e.g. wired or wireless) with the eyewear device 100 (FIG. 8). The software may be provided as an application ("app") to run on the device where the app provides instructions to the eyewear device 100 (e.g. issued via Bluetooth or other wireless or wired communications) to carry out various sequences of activation and deactivation of the various independently-controllable regions 120 of the lens or lenses 110.

In particular embodiments the sequences may be used to simulate conditions associated with opioid use including divided attention and nodding out. For example, a sequence of activations and deactivations of the independently-controllable regions 120 of the lenses 110 can be used to obstruct part or all of the field of vision of the user in one or both eyes for brief or extended periods of time to simulate divided attention: a user who experiences this sequence will find it difficult to focus on tasks in front of them, such as tasks associated with the activity board 300 such as assembling a puzzle. In other embodiments most or all of the independently-controllable regions 120 of the lenses 110 may be activated such that the lenses 110 are mostly or completely made opaque in order to obstruct the user's vision, simulating nodding out.

In some embodiments a timer may be provided to be used as part of the instructional or educational use of the eyewear device 100 and activity board 300 and in one particular embodiment the software (e.g. the app) includes a timer which may be integrated with the control of the sequences of activation and deactivation of the various independently-controllable regions 120 of the lens or lenses 110. In other embodiments a timer may be provided separately from the software (e.g. as a separate handheld timer device).

In practice, a user may put on the eyewear device 100 and optionally attach weights 400 to one or both arms or hands and subsequently attempt to complete an activity on the activity board 300 such as assembling puzzle pieces to produce the image on the board. The user or another person (e.g. an instructor or facilitator) may activate the software to begin one or more sequences of activation and deactivation of the various independently-controllable regions 120 of the lens or lenses 110 to simulate conditions such as divided attention and nodding out. In addition, the overlays 200 on the lenses 110 which reduce or block peripheral vision may simulate contrast sensitivity while the weights 400 simulate heavy extremities.

A time may be measured using the timer to determine how long it takes the user to complete the task, such as correctly assembling the puzzle, while being subject to the simulated opioid impairment. This time may be compared to a benchmark time which indicates how long the task should take without impairment; in one embodiment the benchmark time may be based on the user's completion of the same task under non-impaired conditions, e.g. without wearing the eyewear device 100 (with or without the overlays 200) and/or weights 400. The user can then see by the difference in the amount of time it takes to complete the task under impaired compared to non-impaired conditions how opioid impairment can make a person's life more difficult. In other embodiments the user may simply try to complete the task within a predetermined time limit, e.g. thirty seconds, 1 minute, 2 minutes, etc., to gain the experience of the difficulty of conducting a relatively easy task such as assembling a puzzle with relatively few pieces while being subjected to simulated opioid impairment.

The lower portion of FIG. 7 shows an embodiment of a computer system 500 that can be used to send control information to the eyewear device 100 (e.g. via wired or wireless communication 505) in accordance with embodiments of the disclosed subject matter. As shown in FIG. 7, in some embodiments, computer system 500 can include a processor 510, a user interface and/or display 540, one or more communication systems 530, and memory 520. In some embodiments, processor 510 can be any suitable hardware processor or combination of processors, such as a central processing unit (CPU), a graphics processing unit (GPU), a microcontroller (MCU), a field programmable gate array (FPGA), an application-specific integrated circuit (ASIC), a dedicated image processor, etc. In some embodiments, input(s) and/or display 540 can include any suitable display device(s), such as a computer monitor, a touchscreen, a television, etc., and/or input devices and/or sensors that can be used to receive user input, such as a keyboard, one or more physical buttons with dedicated functions, one or more physical buttons with software programmable functions, a mouse, a touchscreen, a microphone, a gaze tracking system, motion sensors, etc.

In some embodiments, communications systems 530 can include any suitable hardware, firmware, and/or software for communicating information over a communication network and/or any other suitable communication networks. For example, communications systems 530 can include one or more transceivers, one or more communication chips and/or chip sets, etc. In a more particular example, communications systems 530 can include hardware, firmware and/or software that can be used to establish a Wi-Fi connection, a Bluetooth connection, a cellular connection, an Ethernet connection, an optical connection, etc.

In some embodiments, memory 520 can include any suitable storage device or devices that can be used to store instructions, values, etc., that can be used, for example, by hardware processor 510 to process image data generated by one or more optical detectors, to present content using input(s)/display 540, to communicate with an external computing device via communications system(s) 530, etc. Memory 520 can include any suitable volatile memory, non-volatile memory, storage, any other suitable type of storage medium, or any suitable combination thereof. For example, memory 520 can include RAM, ROM, EEPROM, one or more flash drives, one or more hard disks, one or more solid state drives, one or more optical drives, etc. In some embodiments, memory 520 can have encoded thereon a computer program for carrying out one or more embodiments of the disclosed procedures.

Various embodiments may be carried out with a system that includes a memory (such as memory 520) in communication with a processor (such as processor 510), the memory having stored thereon a set of instructions which, when executed by the processor, cause the processor to carry out steps of various embodiments of the procedures disclosed herein. In some embodiments, the memory may include any suitable computer readable media which can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RANI, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 9:
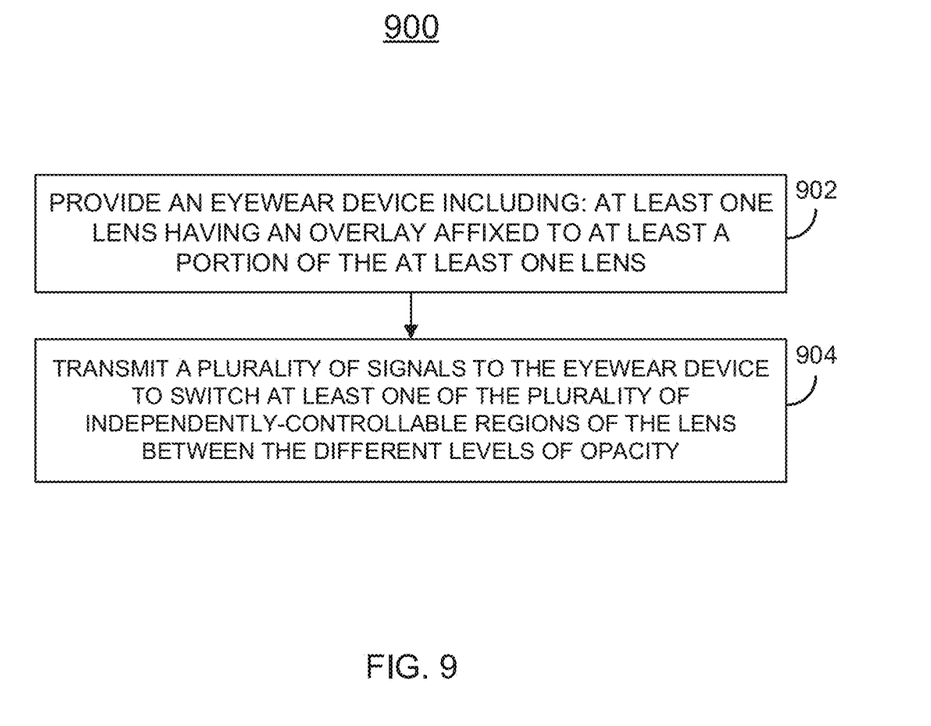
FIG. 9 shows a flow chart of a process for demonstrating an effect of opioid compounds to a user in accordance with some embodiments of the disclosed subject matter.

FIG. 9 shows an example 900 of a process for demonstrating an effect of opioid compounds to a user in accordance with some embodiments of the disclosed subject matter. As shown in FIG. 9, at 902, process 900 can provide an eyewear device including at least one lens having an overlay affixed to at least a portion of the at least one lens. The overlay may include a pattern that at least partially obscures a peripheral region of the at least one lens. The at least one lens includes a plurality of independently-controllable regions configured to be switched between different levels of opacity.

At 904, process 900 can transmit, by a processor in communication with the eyewear device, a plurality of signals to the eyewear device to switch at least one of the plurality of independently-controllable regions of the lens between the different levels of opacity.

It should be understood that the above described steps of the processes of FIG. 9 can be executed or performed in any order or sequence not limited to the order and sequence shown and described in the figures. Also, some of the above steps of the processes of FIG. 9 can be executed or performed substantially simultaneously where appropriate or in parallel to reduce latency and processing times.

The disclosed systems and methods for demonstrating the effect of opioid compounds on a user may be used as part of an educational program to inform various groups (e.g. students in middle or high school or college or adults, and/or the parents of such students) about the dangers and consequences of opioid usage and addiction. The methods and systems help to simulate certain experiences felt by people who are using opioid compounds, which can act preventatively to warn users of the dangers of opioid use as well as to create empathy for those who are currently struggling with opioid addiction and the difficulties they face in their daily lives.

The present invention has been described in terms of one or more preferred embodiments, and it should be appreciated that many equivalents, alternatives, variations, and modifications, aside from those expressly stated, are possible and within the scope of the invention.

What is claimed is:

1. A system for demonstrating an effect of opioid compounds to a user, comprising:
    an eyewear device including at least one lens having an overlay affixed to at least a portion of the at least one lens,
        the overlay comprising a pattern that at least partially obscures a peripheral region of the at least one lens,
        the at least one lens comprising a plurality of independently-controllable regions configured to be switched between different levels of opacity, and
        the overlay comprising concentric patterning including a central opening aligned with a junction at which the independently-controllable regions converge;
    a processor in communication with the eyewear device; and
    a memory in communication with the processor having stored thereon a set of instructions which, when executed by the processor, cause the processor to:
        transmit a plurality of signals to the eyewear device to switch at least one of the plurality of independently-controllable regions of the lens between the different levels of opacity.

2. The system of claim 1, wherein the processor is further caused by the instructions to:
    operate a timer to record an amount of elapsed time while the user interacts with an activity board.

3. The system of claim 2, wherein the activity board comprises a puzzle.

4. The system of claim 3, wherein the processor, when operating the timer, is further caused by the instructions to:
    operate the timer to record the amount of elapsed time while the user interacts with the activity board to assemble the puzzle.

5. The system of claim 4, wherein the plurality of independently-controllable regions of the lens comprises four independently-controllable regions.

6. The system of claim 1, further comprising at least one weight configured to attach to an arm or hand of the user.

7. The system of claim 1, further comprising a smartphone application comprising the set of instructions to be executed by the processor.

8. The system of claim 1, wherein the processor communicates with the eyewear device using radio frequency communications.

9. The system of claim 1, wherein the processor, when transmitting the plurality of signals, is further caused by the instructions to:
    transmit the plurality of signals to switch at least one of the plurality of independently-controllable regions of the lens between the different levels of opacity in a pattern to divide attention of the user while the user interacts with an activity board.

10. The system of claim 1, wherein the processor, when transmitting the plurality of signals, is further caused by the instructions to:
    transmit the plurality of signals to switch all of the plurality of independently-controllable regions of the lens into an opaque state during a single time interval to simulate the user nodding off while the user interacts with an activity board.

11. A method for demonstrating an effect of opioid compounds to a user, comprising:
    providing an eyewear device including:
        at least one lens having an overlay affixed to at least a portion of the at least one lens,
            the overlay comprising a pattern that at least partially obscures a peripheral region of the at least one lens,
            the at least one lens comprising a plurality of independently-controllable regions configured to be switched between different levels of opacity, and
            the overlay comprising concentric patterning including a central opening aligned with a junction at which the independently-controllable regions converge; and
    transmitting, by a processor in communication with the eyewear device, a plurality of signals to the eyewear device to switch at least one of the plurality of independently-controllable regions of the lens between the different levels of opacity.

12. The method of claim 11, further comprising:
    operating a timer to record an amount of elapsed time while the user interacts with an activity board.

13. The method of claim 12, wherein the activity board comprises a puzzle.

14. The method of claim 13, wherein operating the timer further comprises:
    operating the timer to record the amount of elapsed time while the user interacts with the activity board to assemble the puzzle.

15. The method of claim 14, wherein the plurality of independently-controllable regions of the lens comprises four independently-controllable regions.

16. The method of claim 11, further comprising attaching at least one weight to an arm or hand of the user.

17. The method of claim 11, wherein transmitting the plurality of signals to the eyewear device further comprises:
    transmitting the plurality of signals to the eyewear device using a smartphone application.

18. The method of claim 11, wherein transmitting the plurality of signals to the eyewear device further comprises:
    transmitting the plurality of signals to the eyewear device using radio frequency communications.

19. The method of claim 11, wherein transmitting the plurality of signals further comprises:
    transmitting the plurality of signals to switch at least one of the plurality of independently-controllable regions of the lens between the different levels of opacity in a pattern to divide attention of the user while the user interacts with an activity board.

20. The method of claim 11, wherein transmitting the plurality of signals further comprises:
    transmitting the plurality of signals to switch all of the plurality of independently-controllable regions of the lens into an opaque state during a single time interval to simulate the user nodding off while the user interacts with an activity board.

21. A kit for demonstrating an effect of opioid compounds to a user, comprising:
- an eyewear device including at least one lens having an overlay affixed to at least a portion of the at least one lens,
  - the overlay comprising a pattern that at least partially obscures a peripheral region of the at least one lens,
  - the at least one lens comprising a plurality of independently-controllable regions configured to be switched between different levels of opacity, and
  - the overlay comprising concentric patterning including a central opening aligned with a junction at which the independently-controllable regions converge;
- a timer;
- an activity board; and
- at least one weight configured to attach to an arm or hand of the user.

* * * * *

UNITED STATES PATENT AND TRADEMARK OFFICE
CERTIFICATE OF CORRECTION

| | |
|---|---|
| PATENT NO. | : 11,678,841 B1 |
| APPLICATION NO. | : 17/106540 |
| DATED | : June 20, 2023 |
| INVENTOR(S) | : Timothy Jorgensen et al. |

It is certified that error appears in the above-identified patent and that said Letters Patent is hereby corrected as shown below:

In the Specification

Column 10, Line 36, "RANI" should be --RAM--.

Signed and Sealed this
Twenty-second Day of August, 2023

*Katherine Kelly Vidal*

Katherine Kelly Vidal
*Director of the United States Patent and Trademark Office*